United States Patent [19]

Ackrell

[11] 4,104,280
[45] Aug. 1, 1978

[54] DIBENZO [b.f]THIEPIN AND DIBENZO[b.f]OXEPIN DERIVATIVES

[75] Inventor: Jack Ackrell, Palo Alto, Calif.

[73] Assignee: Syntex (U.S.A.) Inc., Palo Alto, Calif.

[21] Appl. No.: 765,493

[22] Filed: Feb. 4, 1977

[51] Int. Cl.² .................. C07D 337/14; C07D 313/14
[52] U.S. Cl. .......................... 260/327 B; 260/293.57; 260/293.58; 260/333; 424/250; 424/253; 424/267; 424/273 R; 424/275; 424/278; 548/335; 544/268; 544/375
[58] Field of Search ............... 260/327 B, 333, 515 R

[56] References Cited

U.S. PATENT DOCUMENTS

| | | | |
|---|---|---|---|
| 3,598,867 | 8/1971 | Fouche | 260/515 |
| 3,946,036 | 3/1976 | Gadient | 260/327 B |
| 4,025,640 | 5/1977 | McFadden | 424/275 |

*Primary Examiner*—Cecilia M. Jaisle

*Attorney, Agent, or Firm*—Gerard A. Blaufarb

[57] ABSTRACT

Novel dibenzo[b.f]thiepin and oxepin compounds of the formula

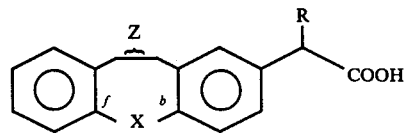

and the pharmaceutically acceptable esters and salts thereof, wherein R is hydrogen or methyl; X is oxygen or $S(O)_n$ in which $n$ is the integer 0, 1 or 2 and Z is a single or double bond, provided that when Z is a double bond X is not SO, and when R is methyl the compounds are (dl) mixtures, and methods for the production thereof.

23 Claims, No Drawings

DIBENZO [b.f]THIEPIN AND DIBENZO[B.F]OXEPIN DERIVATIVES

The present invention relates to novel dibenzo[b.f]-thiepin and dibenzo[b.f]oxepin derivatives, and to processes for the production thereof.

These novel compounds can be represented by the following formula:

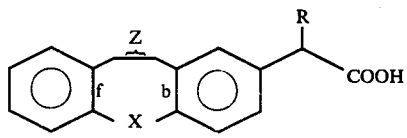

wherein

R is hydrogen or methyl;

X is oxygen or $S(O)_n$, in which $n$ is the integer 0, 1 or 2, and Z is a single or double bond, provided that when Z is a double bond X is not SO, and the pharmaceutically acceptable esters and salts thereof.

The compounds of the present invention in which R is methyl possess an asymmetric center, and thus exist as pairs of enantiomorphs (optical isomers) i.e., as (dl) mixtures. Each enantiomorph, as well as the (dl) mixtures thereof are included within the present invention.

As used in this specification and claims, the term "pharmaceutically acceptable esters" denotes those ester groups conventionally employed in this art, preferably those derived from hydrocarbon carboxylic acids or their salts. The term "hydrocarbon carboxylic acid" refers to both substituted and unsubstituted hydrocarbon carboxylic acids. These acids can be completely saturated or possess varying degrees of unsaturation (including aromatic), can be of straight chain, branched chain, or cyclic structure and preferably contain from 1 to 12 carbon atoms. Typical conventional esters, expressed as the radical, thus included within the scope of the term as defined above are acetate, propionate, 2-methylpropionate, butyrate, pentanoate, hexanoate, heptanoate, octanoate, nonanoate, dodecanoate, benzoate, 2-acetoxybenzoate, salicylate, phenylacetate, diethylacetate, trimethylacetate, t-butylacetate, cyclohexylacetate, cyclopentylpropionate, adamantoate, bicyclo[2.2.2]octyl carboxylate, hemisuccinate, hemiadipate, hemi-$\beta,\beta$-dimethylglutarate, and the like.

The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The novel dibenzo[b.f]thiepin acetic acid compounds of the present invention can be prepared by a process illustrated by the following reaction sequence:

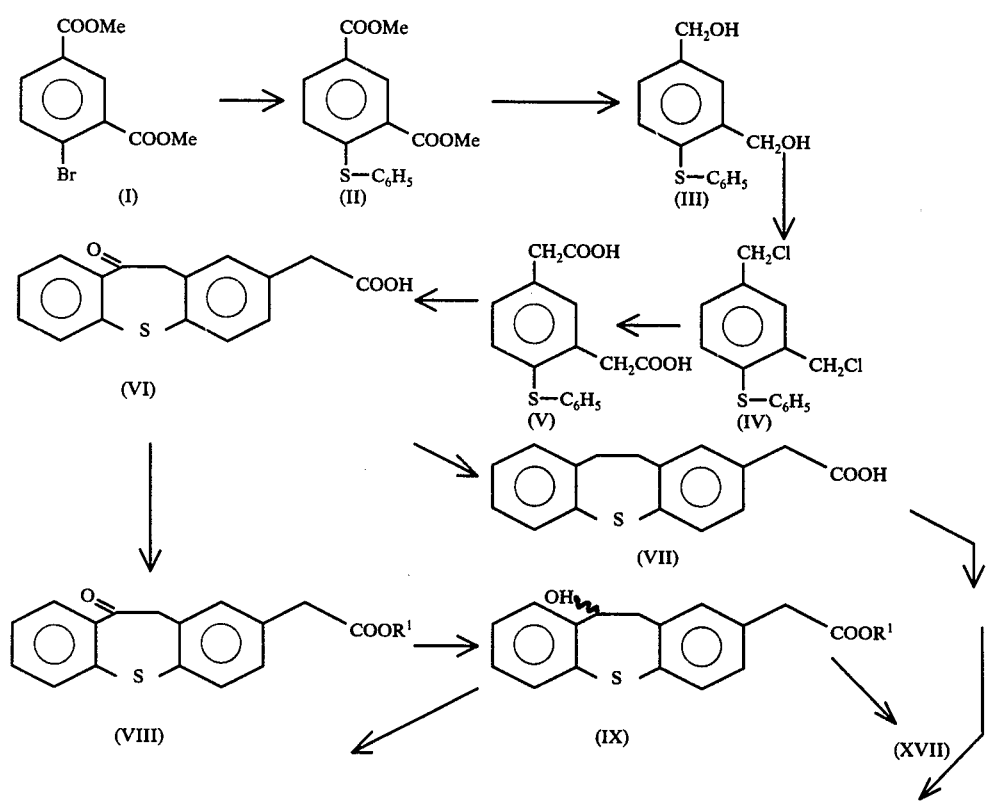

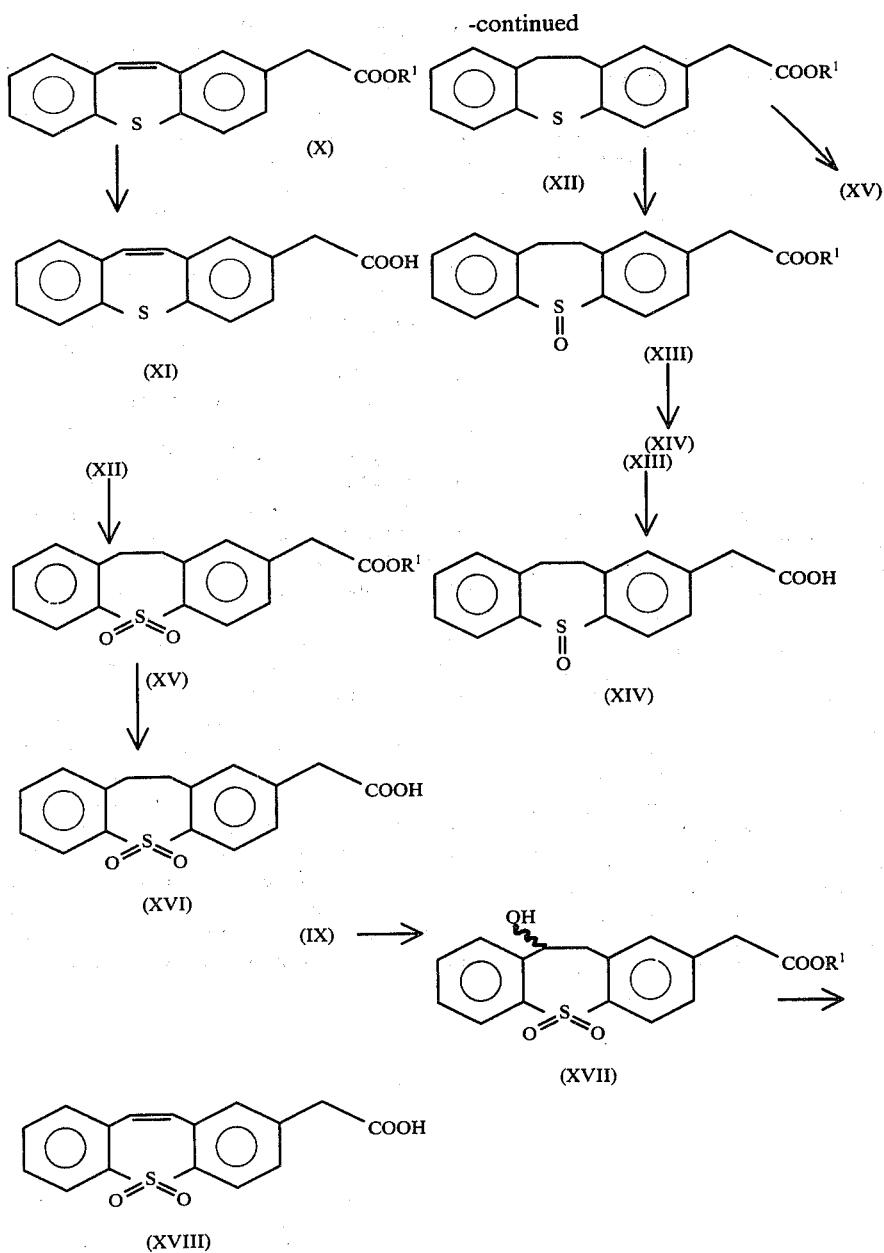

wherein $R^1$ is a lower alkyl group of 1 to 3 carbon atoms, preferably methyl.

In practicing the process outlined above the starting material, dimethyl 4-bromoisophthalate (I) is treated with an excess of thiophenol in the presence of an alkali metal hydride such as sodium hydride or potassium hydride in an inert organic solvent, e.g., dimethylformamide, dimethoxyethane, dimethyl sulfoxide and the like. The reaction is conducted at reflux temperature, for from about 10 hours to about 24 hours, preferably for about 16 to 18 hours, to produce dimethyl 4-(phenylthio)isophthalate (II).

Reduction of compound (II) with a double metal hydride such as lithium aluminum hydride, lithium borohydride, sodium trimethoxyborohydride and the like, in a suitable inert organic solvent e.g., tetrahydrofuran, dimethoxyethane, diethyl ether and the like, produces 2,4-bis-(hydroxymethyl)diphenyl sulfide (III). The reaction is conducted at a temperature of from about 0° to about 50° C, for a period of time sufficient to complete the reaction, ranging from about 30 minutes to about 3 hours. In the preferred embodiments, the reaction is carried out using lithium aluminum hydride as reagent and tetrahydrofuran as solvent, at about room temperature or under slight heating for about 30 minutes to about 90 minutes.

2,4-bis-(chloromethyl)diphenyl sulfide (IV) is obtained by treatment of compound (III) with thionyl chloride in an anhydrous inert organic solvent such as methylene chloride, benzene and the like, at a temperature of from about room temperature to reflux, for about 20 minutes to about 16 hours, the reaction time depending upon the temperature at which the reaction takes place. Preferably the reaction is conducted at reflux temperature for about 30 minutes, using methylene chloride as solvent.

Upon reaction of compound (IV) with an alkali metal cyanide such as sodium cyanide, potassium cyanide or lithium cyanide in an inert organic solvent e.g., dimethylformamide, dimethyl sulfoxide, N-methylpyrrolidone and the like, at a temperature comprised between about 0° C to room temperature, for about 16 hours to about 24 hours, followed by strong acid treatment, i.e., by treatment with a mineral or organic acid such as sulfuric acid, hydrochloric acid, phosphoric acid, perchloric acid, acetic acid and the like, or mixtures thereof, there is obtained 2,4-bis-(carboxymethyl)diphenylsulfide (V). Preferably, this reaction is effected using a (1:1) mixture of acetic acid and 85% aqueous phosphoric acid, at reflux temperature for about 16 to 24 hours.

Compound (V) is converted into 10,11-dihydrodibenzo[b.f]thiepin-10-one-2-acetic acid (VI) via conventional formation of the diacid chloride using oxalyl chloride at about room temperature for about 18 to about 30 hours. The diacid chloride thus prepared is then converted into 10,11-dihydrodibenzo[b.f]thiepin-10-one-2-acetic acid (VI) by cyclization with aluminum chloride and nitromethane in the presence of a suitable inert organic solvent, such as a chlorinated hydrocarbon, e.g., methylene chloride, chloroform, carbon tetrachloride and the like, at a temperature of from about -40° C to about 25° C, for about 30 minutes to about 4 hours, preferably at about room temperature for about 2 hours.

Reduction of compound (VI) with zinc amalgam in an aromatic hydrocarbon as solvent, e.g., toluene and xylene, in the presence of a strong mineral acid, e.g., sulfuric acid or hydrochloric acid, produces 10,11-dihydrodibenzo[b.f]thiepin-2-acetic acid (VII). The reaction is conducted at reflux temperature, for about 1 hour to about 3 hours. The preferred solvent is toluene.

The free acid compounds of formulas (VI) and (VII) can be converted into the corresponding alkyl esters (VIII and XII respectively) by methods known to those skilled in the art, using an ethereal diazoalkane such as diazomethane and diazoethane, with the desired lower alkyl iodide in the presence of lithium carbonate or potassium carbonate, at room temperature, or with the desired lower alkanol in the presence of catalytic amounts of sulfuric acid at reflux temperature, or hydrogen chloride, at room temperature.

Reduction of a compound (VIII) with a double metal hydride such as sodium borohydride, lithium borohydride and the like in a suitable organic solvent such as dimethoxyethane or a lower aliphatic alcohol, e.g., methanol, at about 10° to about 40° C, for about 2 to about 24 hours, followed by dehydration of the thus produced corresponding 10-hydroxy intermediate (IX) by refluxing with a trace of a strong mineral or organic acid, using particularly 70% perchloric acid, produces the corresponding alkyl ester of dibenzo[b.f]thiepin-2-acetic acid (X) which is hydrolyzed to the free acid (XI) by conventional base treatment. Generally, this reaction is effected by treating (X) with an alkali metal hydroxide or an alkali metal carbonate, such as sodium hydroxide, potassium hydroxide, sodium carbonate and potassium carbonate, in a lower aqueous aliphatic alcohol as solvent, e.g., methanol, ethanol, isopropanol and the like, at a temperature of from about 40° C to the reflux temperature of the solvent used, for from about 45 minutes to about 3 hours. Preferably, this hydrolysis is effected with potassium carbonate in aqueous methanol, at reflux temperature for about 1 hour.

Oxidation of a compound (XII) with 1-1.1 molar equivalents of a peracid, such as m-chloroperbenzoic acid, p-nitrobenzoic acid, perphthalic acid, peracetic acid, and the like, affords the corresponding sulfo derivative, i.e., alkyl 10,11-dihydrodibenzo[b.f]thiepin-2-acetate-S-oxide (XIII). The oxidation is carried out in an inert organic solvent such as diethyl ether, methylene chloride, chloroform, dimethoxyethane and the like, at a temperature of from about −10° C to room temperature, for a period of time sufficient to complete the reaction, ranging from about 5 minutes to about 1 hour. In the preferred embodiments, the oxidation is effected with m-chloroperbenzoic acid in dimethoxyethane solution at about 0° C, for about 5 minutes to about 10 minutes.

Basic hydrolysis of the alkyl ester group, preferably with methanolic potassium carbonate affords the free acid of formula (XIV), namely 10,11-dihydrodibenzo[b.f]thiepin-2-acetic acid-S-oxide.

When the oxidation of compound (XII) is carried out using at least 2 molar equivalents of the peracid there is obtained the corresponding esterified sulfone of formula (XV), which is converted into the free acid, 10,11-dihydrodibenzo[b.f]thiepin-2-acetic acid-S,S-dioxide (XVI), by acid hydrolysis using particularly a mixture of formic acid and p-toluenesulfonic acid. The reaction is conducted at reflux temperature, for about 12 to about 24 hours, preferably for about 18 hours.

Oxidation of compound (IX) with at least two molar equivalents of a peracid such as m-chloroperbenzoic acid, perphthalic acid, perbenzoic acid, peracetic acid and the like in a suitable inert organic solvent such as methylene chloride, diethyl ether, chloroform, dimethoxyethane and the like, at a temperature of from about -10° C to room temperature, for about 5 minutes to about 1 hour affords a product containing the corresponding sulfone, (XVII), which upon treatment with formic acid-p-toluenesulfonic acid, at reflux temperature for about 2 to about 6 hours, preferably for about 3 hours, undergoes simultaneous dehydration and hydrolysis of the alkyl ester group, to produce dibenzo[b.f.]thiepin-2-acetic acid-S,S-dioxide (XVIII).

The dibenzo[b.f]oxepin-2-acetic acid compounds can be prepared by a process illustrated by the following reaction sequence:

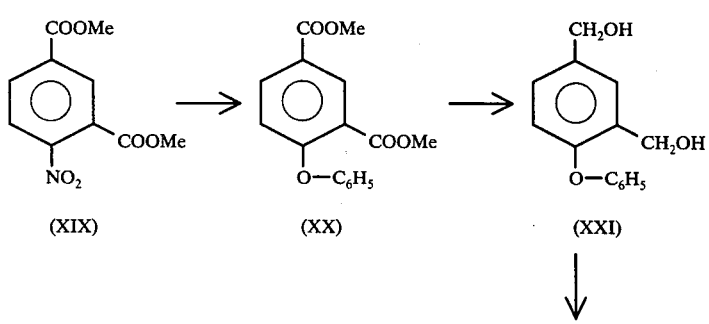

-continued

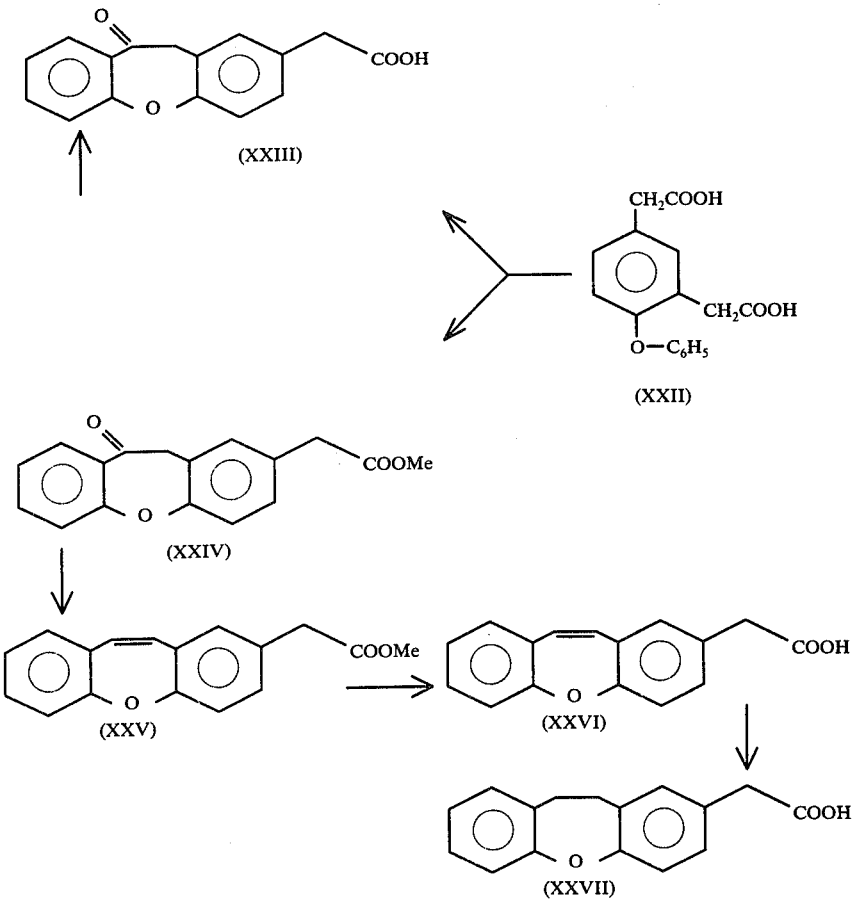

In practicing the process outlined above, the starting material, dimethyl 4-nitroisophthalate (XIX) is treated with an excess of phenol in the presence of an alkali metal hydride such as sodium hydride or potassium hydride in an inert organic solvent, e.g., dimethylformamide, dimethyl sulfoxide and the like, to produce dimethyl 4-phenoxyisophthalate (XX). The reaction is effected at a temperature between room temperature and reflux, for from about 6 to about 16 hours, the reaction time depending upon the temperature at which the reaction takes place. In the preferred embodiments, the reaction is conducted at room temperature, for about 12 hours.

Reduction of compound (XX) with a double metal hydride such as lithium aluminum hydride, lithium borohydride, sodium trimethoxyborohydride and the like in a suitable inert organic solvent, e.g., tetrahydrofuran, dimethoxyethane and the like, produces 2,4-bis-(hydroxymethyl)diphenyl ether (compound XXI). The reaction is conducted at a temperature of from about 0° C to about 50° C, for a period of time sufficient to complete the reaction, ranging from about 30 minutes to about 90 minutes. In the preferred embodiments, the reaction is carried out using lithium aluminum hydride as reagent and dimethoxyethane as solvent, at room temperature for about 1 hour.

Upon reaction of the foregoing compound (XXI) with thionyl chloride and thereafter with an alkali metal cyanide such as sodium cyanide, potassium cyanide or lithium cyanide in an inert organic solvent e.g., dimethylformamide, dimethyl sulfoxide, N-methylpyrrolidone and the like, at about room temperature for about 16 to about 24 hours, followed by strong acid treatment, i.e., by treatment with a mineral or organic acid such as sulfuric acid, hydrochloric acid, phosphoric acid, perchloric acid, acetic acid and the like, or mixtures thereof, there is obtained a crude product containing 2,4-bis-(carboxymethyl)diphenyl ether (XXII). Typically, this reaction is effected using a (1:1) mixture of acetic acid and 85% aqueous phosphoric acid, at reflux temperature for about 16 to about 24 hours, and the crude material is further purified via formation of the potassium salt.

By conventional treatment of compound (XXII) with oxalyl chloride there is obtained the acid chloride derivative, which is submitted to a cyclization using aluminum chloride and nitromethane in a chlorinated hydrocarbon as solvent, e.g., methylene chloride, chloroform, carbon tetrachloride and the like, at a temperature of from about 0° to about 25° C, for about 10 minutes to about 1 hour, preferably at room temperature for about 30 minutes. The reaction product is then refluxed with methanol for a short period of time, to afford a mixture of 10,11-dihydrodibenzo[b.f]oxepin-10-one-2-acetic acid (XXIII) and its methyl ester (XXIV), which is separated into the free acid and the esterified compound in a conventional manner, via formation of the sodium or potassium salt of the free acid, soluble in water, and liberation of the acid (XXIII) therefrom by treatment with a strong mineral acid, e.g., sulfuric acid or hydrochloric acid.

The methyl ester (XXIV) can be converted into the free acid (XXIII) by conventional hydrolysis with an alkali metal hydroxide or alkali metal carbonate in an aqueous aliphatic alcohol, e.g., methanol or ethanol, preferably at reflux temperature for about 30 minutes to about 2 hours.

Methyl dibenzo[b.f]oxepin-2-acetate (XXV) can be prepared by sodium borohydride reduction of compound (XXIV) followed by dehydration of the 10-hydroxy intermediate with traces of a strong mineral or organic acid, using particularly 70% aqueous perchloric acid in dimethoxyethane solution.

Basic hydrolysis of compound (XXV) affords the free acid, namely dibenzo[b.f]oxepin-2-acetic acid (XXVI). This reaction is preferably carried out using aqueous methanolic potassium hydroxide at reflux temperature for about 10 minutes.

Upon catalytic hydrogenation of the double bond in compound (XXVI) there is obtained 10,11-dihydrodibenzo[b.f]oxepin-2-acetic acid (XXVII). This reduction is carried out in the presence of a palladium catalyst such as 10% palladium on charcoal, in an inert organic solvent, e.g., dimethoxyethane, tetrahydrofuran, ethyl acetate and the like.

The benzo[b.f]thiepin and benzo[b.f]oxepinpropionic acid derivatives can be prepared by a process illustrated by the following reaction sequence:

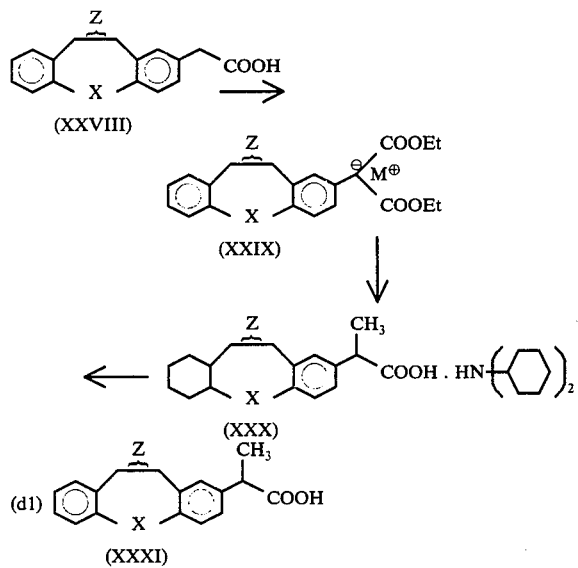

wherein X and Z are as defined above, and M⊕ is an alkali metal cation.

The starting material i.e., a benzothiepin or benzoxepin acetic acid compound of formula (XXVIII), which formula is a composite of compounds (VII), (XI), (XIV), (XVI), (XVIII), (XXVI) and (XXVII) is converted into the corresponding methyl ester by conventional treatment with diazomethane, and thereafter submitted to carboethoxylation with diethyl carbonate in the presence of an alkali metal alkoxide, in an inert organic solvent or mixtures of solvents, to give the diethyl malonate intermediate of formula (XXIX). Suitable alkali metal alkoxides are sodium methoxide, sodium ethoxide, potassium isopropoxide, potassium t-butoxide and the like, using a solvent medium comprising preferably an aromatic hydrocarbon, e.g., benzene, toluene or xylene, and the alcohol corresponding to the alkoxide used as cosolvent. The reaction is conducted at reflux temperature, for about 8 to about 24 hours. Typically, the reaction is conducted in the presence of potassium t-butoxide, in a mixture of toluene-t-butanol as solvent, refluxing the reaction mixture for about 12 hours.

The "anion" thus formed (XXIX) is then alkylated in the same solvent system with a methyl halide, e.g., methyl iodide, at reflux temperature for a further period of about 2 to about 12 hours; the reaction is generally complete within about 4 hours. There are used from 1.0 to 1.5 molar equivalents of methyl iodide per molar equivalent of starting compound. The reaction product is thereafter treated with potassium hydroxide in aqueous methanol, at reflux temperature for about 30 minutes to cleave the diethyl malonate moiety, and the free acid thus obtained is purified via formation of the corresponding dicyclohexylammonium salt (XXX), which upon treatment with a strong mineral acid, e.g., hydrochloric acid, sulfuric acid and the like, in a suitable organic solvent, e.g., benzene, methylene chloride, diethyl ether and the like, at a temperature of from about 0° to about 40° C, affords readily the free acid (XXXI) in pure form.

Alternatively, the free 2-(10,11-dihydrodibenzo[b.f]-thiepin-2-yl)propionic acid (XXXI, X = S, Z = single bond) can be converted into the sulfoxide (XXXI, X = SO, Z = single bond) via formation of the methyl ester, oxidation with one molar equivalent of a peracid and base hydrolysis of the methyl ester protecting group, or into the sulfone (XXI, X = SO$_2$, Z = single bond) when using at least 2 molar equivalents of the peracid, as described hereinbefore with regard to the benzothiepin acetic acid series (XII→XIV and XII→XVI, respectively).

Upon their preparation, the free acids of the present invention represented by formula (A) can be converted into the corresponding esters and pharmaceutically acceptable salts thereof.

The compounds of Formulas (VII), (XI), (XIV), (XVII), and (XVIII) can be converted into esters of the present invention other than the lower alkyl esters by treatment with an alcohol reagent corresponding to the desired ester, in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent like hexane, iso-octane, decane, cyclohexane, benzene, toluene, xylene; a halogenated hydrocarbon solvent like methylene chloride, chloroform, dichloroethane; or an ether solvent like diethyl ether, dibutyl ether, dioxane, tetrahydrofuran. In the case where the alcohol reagent is a solid, the reaction is preferably conducted in a non-aqueous liquid inert organic solvent. The reaction is conducted at from about 0° C. to the reflux temperature of the reaction mixture, preferably from 15° to about 35° C.

The compounds of formulas (XXVI), (XXVII) and (XXXI) can be converted into the corresponding esters of the present invention by any of the esterification methods described hereinbefore.

The salt derivatives of the compounds of Formula (A) are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° to about 100° C, preferably at room temperature. Typical inert, water-miscible organic solvents include methanol, ethanol, isopropanol, butanol, acetone, dioxane or tetrahydrofuran. The molar ratio of compounds of Formula (A) to base used are chosen to provide the ratio desired for any particular salt. For preparing, for example, the calcium salts or magnesium salts, the free acid starting material can be treated with at least one half molar equivalent of pharmaceutically acceptable base to yield a neutral salt. When the aluminum salts of the compound of Formula (A) are prepared, at least one-third molar equivalent of the pharmaceutically acceptable base are employed if a neutral salt product is desired.

In the preferred procedure, the calcium salts and magnesium salts of the compounds of Formula (A) can be prepared by treating the corresponding sodium or potassium salts with at least one-half molar equivalent of calcium chloride, or magnesium chloride respectively, in an aqueous solution, alone or in combination with an inert water-miscible organic solvent, at a temperature of from about 20° to about 100° C. Preferably, the aluminum salts of the compounds of Formula (A) can be prepared by treating the corresponding free acids with at least one-third molar equivalent of an aluminum alkoxide, such as aluminum triethoxide, aluminum tripropoxide and the like, in a hydrocarbon solvent, such as benzene, xylene, cyclohexane, and the like, at a temperature of from 20° to about 115° C. Similar procedures can be used to prepare salts of inorganic bases which are not sufficiently soluble for easy reaction.

It is to be understood that the isolation and purification of the compounds described herein can be effected by any separation or purification procedure, such as, for example, extraction, filtration, evaporation, distillation, crystallization, thin-layer chromatography or column chromatography, or a combination of these procedures. Illustrations of suitable separation and isolation procedures can be had by reference to the examples described herein below. However, other equivalent separation or isolation procedures could, of course, also be used.

The compounds of Formula (A) and the pharmaceutically acceptable esters and salts thereof are useful as anti-inflammatory agent, platelet aggregation inhibitors, fibrinolytic agents, analgetic agents, and as smooth muscle relaxants. They can be used both prophylactically and therapeutically.

The compounds of Formula (A) and the pharmaceutically acceptable esters and salts thereof exhibit anti-inflammatory, analgesic and anti-pyretic activities. Accordingly, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compounds of Formula (A) and the pharmaceutically acceptable esters and salts thereof, in an appropriate pharmaceutical composition can be via any of the accepted modes of administration of agents for the treatment of inflammation, pain or pyrexia, or the prophylaxis thereof. Thus, administration can be for example, orally, parenterally, or topically, in the form of solid, semi-solid or liquid dosage forms, such as, for example, tablets, suppositories, pills, capsules, powders, liquids, suspensions, creams, lotions, ointments, or the like, preferably in unit dosage forms suitable for simple administration of precise dosages. The compositions will include a conventional pharmaceutical carrier or excipient and an active compound of Formula (A) and the pharmaceutically acceptable esters and salts thereof and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 0.05 mg. to 20 mg. of the active compound of Formula (A) and the pharmaceutically acceptable esters and salts thereof per kilogram of body weight is used. Most conditions respond to treatment comprising a dosage level of the order of 0.25 mg. to 6 mg. per kilogram of body weight per day. For such oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compound of Formula (A) and the pharmaceutically acceptable esters and salts thereof, may be formulated into a suppository using, for example, polyalkylene glycols, for example, propylene glycol, as the carrier. Liquid pharmaceutically administerable compositions can, for example, be prepared by dissolving, dispersing, etc. an active compound of Formula (A) and the pharmaceutically acceptable esters and salts thereof and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine, oleate, etc.

Actual methods of preparing such dosage forms are known, or will be apparent, to those skilled in this art; for example, see Remington's Pharmaceutical Sciences, Mack Publishing Company, Easton, Pa., 14th. Edition, 1970. The composition to be administered will, in any event, contain a quantity of the active compound(s) in a pharmaceutically effective amount for relief of the particular condition being treated in accordance with the teachings of this invention.

The compounds of Formula (A) and the pharmaceutically acceptable esters and salts thereof, described above are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formula (A) and the pharmaceutically acceptable esters and salts thereof, are used as agents for delaying the onset of, or for postponing, parturition. As used in this application, the phrase "to delay the onset of parturition" is intended to cover that delay in parturition caused by the administration of the compounds of Formula (A) and the pharmaceutically acceptable esters and salts thereof at any time before uterine muscle contractions have begun. Thus, it is intended that the aforementioned phrase covers abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formula (A) and the pharmaceutically acceptable esters and salts thereof after uterine muscle contractions have begun. The condition of the patient, including the time within the gestation period when the contractions have begun, the severity of the contractions and how long the contractions have taken place will affect the results achieved with the administration of the compounds of Formula (A) and the pharmaceutically acceptable esters and salts thereof. For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formula (A) and the pharmaceutically acceptable esters and salts thereof, for the purposes set forth herein, should be consistent with the best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formula (A) and the pharmaceutically acceptable esters and salts thereof, or a pharmaceutical composition containing a compound of Formula (A) and the pharmaceutically acceptable esters and salts thereof, is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, sucrose, magnesium carbonate, and the like. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 14th. Edition, 1970. The composition or formulation to be administered will, in any event, contain a quantity of the active compound(s) in an amount effective to delay the onset of parturition or to postpone parturition if uterine contractions have already begun. Generally a daily dose of from 5 mg. to about 250 mg. of the active compound per kilogram of body weight will be administered, with administration being a single daily dose of up to three or four smaller doses regularly given throughout the day. The amount of active compound adminstered will, of course, depend on its relative activity.

The following Examples illustrate the invention but are not intended to limit its scope. All mixture ratios used with regard to liquids refer to volume ratios. When necessary, examples are repeated to provide additional material for subsequent examples.

EXAMPLE 1

To a solution of 3.6 g. of a 57% dispersion of sodium hydride in mineral oil in 80 ml. of dimethylformamide containing 9.3 ml. of thiophenol there are added 20 g. of dimethyl 4-bromoisophthalate, and the resulting mixture is refluxed for 18 hours. It is then cooled and poured into 800 ml. of water, and acidified with 3N aqueous hydrochloric acid. The product is extracted with ether-ethyl acetate (1:1) (3 × 150 ml.) and the combined extracts washed with water (3 × 150 ml.), then with saturated aqueous sodium chloride (100 ml.). The organic layer is dried with anhydrous magnesium sulfate and the solvent is evaporated under reduced pressure. The above procedure is repeated, the two runs combined and distilled at 0.03 mm, to yield 35 g. of dimethyl 4-phenylthioisophthalate (II), b.p. 176°/0.03 mm. The product crystallizes on standing and has a melting point of 65°–67° C after recrystallization from ether-hexane.

EXAMPLE 2

A solution of 35 g. of dimethyl 4-phenylthioisophthalate in 200 ml. of ether is added slowly, over a 1 hour period, to a solution of 7.0 g. of lithium aluminum hydride in 100 ml. of dry tetrahydrofuran and the reaction mixture is maintained at room temperature for 10 minutes further. Excess lithium aluminum hydride is destroyed by the addition of 20 ml. of acetone and then saturated aqueous sodium chloride solution is slowly added until the gray suspension turns white. The precipitated metal salts are filtered off and the filtrate is evaporated to give 25 g. of 2,4-bis-(hydroxymethyl)diphenyl sulfide (III), as an oil, which slowly crystallizes. After crystallization from benzene the product melts at 68–69° C.

EXAMPLE 3

A solution of 60 g. of 2,4-bis-(hydroxymethyl)-diphenyl sulfide in 500 ml. of methylene chloride is treated with 40 ml. of thionyl chloride. The reaction mixture is refluxed for 30 minutes, then poured on ice, and extracted with ether (2 × 200 ml.). The combined extracts are dried and evaporated to dryness to yield an oil containing 2,4-bis(chloromethyl)diphenyl sulfide (IV), which is distilled in vacuum, b.p. 168°/0.1 mm. The oil is dissolved in 100 ml. of dimethylformamide and the so obtained solution is added to a stirred mixture of 21 g. of sodium cyanide and 200 ml. of dimethylformamide, cooled in ice. The reaction mixture is stirred for 18 hours at room temperature, and then poured into 3 l. of water and extracted with ether (3 × 250 ml.). The combined extracts are washed with water (3 × 250 ml.), dried with anhydrous magnesium sulfate and evaporated under reduced pressure to yield a dark yellow oil. The oil is dissolved in a solution containing 200 ml. of acetic acid and 200 ml. of 85% aqueous phosphoric acid. The reaction mixture is refluxed for 18 hours, cooled, and poured into 2 l. of water. The resulting mixture is extracted with ethyl acetate (3 × 100 ml.) and the combined extracts washed with water. The organic layer is then extracted with 10% aqueous sodium carbonate solution (2 × 100 ml.), the aqueous extracts are combined, stirred with 10 g. of charcoal and filtered. The filtrate is heated to about 80° C, slowly acidified with 3N aqueous hydrochloric acid, and allowed to cool. The formed precipitate is collected by filtration, thus obtaining 25 g. of 2,4-bis(carboxymethyl)diphenyl sulfide (V), which has a melting point of 176°–180° C.

EXAMPLE 4

A suspension of 25 g. of 2,4-bis(carboxymethyl)-diphenyl sulfide in 150 ml. of methylene chloride is treated with 25 ml. of oxalyl chloride dissolved in 100 ml. of methylene chloride, and the reaction mixture is stirred for 24 hours at room temperature. The solvent and excess reagent are then evaporated under reduced pressure to yield an oil, which is dissolved in 100 ml. of methylene chloride and added to a solution of 25 g. of aluminum chloride in 12.0 ml. of nitromethane and 200 ml. of methylene chloride, previously cooled to $-40°$ C. The reaction mixture is allowed to warm to room temperature and after 2 hours cooled in ice and vigorously stirred while 30 ml. of saturated aqueous sodium chloride is added. After 24 hours, the mixture is filtered and the filtrate evaporated to dryness. The residue is washed with a little ether and filtered to yield 9 g. of 10,11-dihydrodibenzo[b.f]thiepin-10-one-2-acetic acid (VI), which has a m.p. of 177°–179° C.

EXAMPLE 5

To a mixture of 10 ml. of concentrated hydrochloric acid, 20 ml. of toluene and 5 g. of amalgamated zinc (30 mesh), there is added 500 mg. of 10,11-dihydrodibenzo[b.f]thiepin-10-one-2-acetic acid. The reaction mixture is refluxed for 2 hours, cooled and is then poured into 50 ml. of water. The organic layer is separated, washed with water and dried with anhydrous magnesium sulfate. The solvent is evaporated under reduced pressure and the residue is crystallized from a small volume of ether, to yield 375 mg. of 10,11-dihydrodibenzo[b.f]thiepin-2-acetic acid (VII), which has a melting point of 104° C.

EXAMPLE 6

To a stirred solution of 950 mg. of 10,11-dihydrodibenzo[b.f]thiepin-10-one-2-acetic acid in 15 ml. of dimethylformamide there are added 1.0 g. of potassium carbonate and 0.35 ml. of methyl iodide. After 2 hours at room temperature, the reaction mixture is poured into water (100ml) and extracted with ether-ethyl acetate (3:1) (2 × 25 ml.). The combined extracts are washed with water, dried and the solvents are removed by evaporation under reduced pressure. The residue is crystallized from benzene-hexane (1:1) to yield 950 mg. of methyl 10,11-dihydrodibenzo[b.f]thiepin-10-one-2-acetate (VIII, $R^1$ = Me), which melts at 82° C.

EXAMPLE 7

A solution of 950 mg. of methyl 10,11-dihydrodibenzo[b.f]thiepin-10-one-2-acetate in 10 ml. of dimethoxyethane is treated with 100 mg. of sodium borohydride. The reaction mixture is stirred at room temperature for 4 hours and then is concentrated to about 2.5 ml. by evaporation under reduced pressure, diluted with 30 ml. of water and extracted with ether. The organic layer is separated, dried with anhydrous magnesium sulfate and the solvent evaporated under reduced pressure, to yield an oil which is dissolved in chloroform and filtered through a column of 50 g. of silica gel. Evaporation of the eluate yields methyl 10,11-dihydrodibenzo-[b.f]thiepin-10-ol-2-acetate (IX), as an oil, which is taken up in 50 ml. of dimethoxyethane containing one drop of 70% perchloric acid. The reaction mixture is refluxed for 4 hours, cooled, then poured into 400 ml. of water and extracted with ether. The ethereal extract is dried, evaporated under reduced pressure and the residue is chromatographed on silica gel. The fractions eluted with ethyl acetate:hexane (1:7) afford 550 mg. of methyl dibenzo[b.f]thiepin-2-acetate (X, $R^1$ = Me), as white needles, having a melting point of 100°–101° C after recrystallization from benzene-hexane.

EXAMPLE 8

A solution of 300 mg. of methyl dibenzo[b.f]-thiepin-2-acetate in 20 ml. of methanol is treated with a solution of 100 mg. of potassium carbonate in 0.5 ml. of water. The reaction mixture is refluxed for 1 hour and then evaporated to dryness under reduced pressure. The residue is dissolved in water, the solution is acidified with dilute aqueous hydrochloric acid and extracted with ethyl acetate. The organic layer is dried with anhydrous magnesium sulfate and evaporated to dryness under reduced pressure. The residue is crystallized from ether, to yield 253 mg. of dibenzo[b.f]-thiepin-2-acetic acid (XI), which melts at 144° C.

EXAMPLE 9

A solution of 700 mg. of 10,11-dihydrodibenzo[b.f]-thiepin-2-acetic acid in 25 ml. of methanol is saturated with hydrogen chloride. After two hours at room temperature, the solution is evaporated under reduced pressure and the residue is chromatographed on silica gel using ethyl acetate; hexane (1:7) as eluant to yield 540 mg. of methyl 10,11-dihydrodibenzo[b.f]thiepin-2-acetate (XII, $R^1$ = Me), as an oil, which is dissolved in 20 ml. of methylene chloride. The solution is then treated with 325 mg. of 85% m-chloroperbenzoic acid. After 5 minutes, the solution is washed with 10% aqueous sodium carbonate solution, dried with anhydrous magnesium sulfate and filtered through a column of 10 g. of silica gel, eluting with methylene chloride. Evaporation of the eluate under reduced pressure yields a solid which is crystallized from benzene-hexane, to yield 510 mg. of methyl 10,11-dihydrodibenzo[b.f]thiepin-2-acetate-S-oxide (XIII, $R^1$ = Me), which melts at 115° C.

EXAMPLE 10

A solution of 510 mg. of methyl 10,11-dihydrodibenzo[b.f]thiepin-2-acetate-S-oxide in 20 ml. of methanol is refluxed with 150 mg. of potassium carbonate for 3 hours. The solvent is eliminated under reduced pressure, the residue is dissolved in water and the solution is acidified with dilute aqueous hydrochloric acid. The mixture is extracted with ethyl acetate, the extract is dried with anhydrous magnesium sulfate and the solvent removed under reduced pressure. The residue is dissolved in methylene chloride, and hexane is added to turbidity. After stirring for 15 minutes, the crystallized material is collected by filtration and air dried, to yield 380 mg. of 10,11-dihydrodibenzo[b.f]-thiepin-2-acetic acid-S-oxide (XIV), having a melting point of 169°–170° C.

EXAMPLE 11

A solution of 950 mg. of 10,11-dihydrodibenzo[b.f]-thiepin-2-acetic acid in 50 ml. of methanol is saturated with hydrogen chloride. After 2 hours the reaction mixture is evaporated under reduced pressure and the residue is chromatographed on silica gel using ethyl acetate:hexane (1:7) as eluant to yield methyl 10,11-dihydrodibenzo[b.f]-thiepin-2-acetate (XII, $R^1$ = Me), which is dissolved in 10 ml. of benzene and treated with 900 mg. of 85% m-chloroperbenzoic acid dissolved in 10 ml. of dimethoxyethane. After 5 minutes, 3 ml. of saturated aqueous sodium sulfite is added, followed by 1 ml. of saturated aqueous potassium carbonate. The organic layer is separated, dried with anhydrous magnesium sulfate and filtered through a column of 20 g. of silica gel, eluting with benzene. Evaporation of the eluate under reduced pressure yields a residue which upon recrystallization from chloroform:hexane (1:1) yields 900 mg. of methyl 10,11-dihydrodibenzo[b.f]thiepin-2-acetate-S,S-dioxide (XV, $R^1$ = Me), having a melting point of 103°–105° C.

EXAMPLE 12

Four hundred milligrams of methyl 10,11-dihydrodibenzo[b.f]thiepin-2-acetate-S,S-dioxide is dissolved in 10 ml. of 97% formic acid containing 50 mg. of p-toluenesulfonic acid. The reaction mixture is refluxed for 18 hours, cooled and the volatile acids removed under reduced pressure. The residue is dissolved in ethyl acetate and the solution is washed with water. The organic layer is dried with anhydrous magnesium sulfate, decolorized with charcoal and evaporated under reduced pressure, to yield a residue which is crystallized from benzene, thus obtaining 340 mg. of 10,11-dihydrodibenzo[b.f]thiepin-2-acetic acid-S,S-dioxide (XVI), having a melting point of 161–162° C.

EXAMPLE 13

A solution of 740 mg. of methyl 10,11-dihydrodibenzo[b.f]thiepin-10-one-2-acetate in 20 ml. of dimethoxyethane is treated with 50 mg. of sodium borohydride and is stirred at room temperature for 18 hours. The excess reagent is destroyed by the addition of 1 ml. of acetone, followed by saturated aqueous sodium bisulfate (1 ml.). The organic layer is separated, dried with anhydrous magnesium sulfate and filtered through a column of 10 g. of alumina. Evaporation of the eluate yields an oily product containing methyl 10,11dihydrodibenzo[b.f]thiepin-10-ol-2-acetate (IX, $R^1$ = Me), which is taken up in 20 ml. of methylene chloride and treated with 900 mg. of 85% m-chloroperbenzoic acid. After 5 minutes, the reaction mixture is treated with 2 ml. of saturated aqueous sodium sulfite solution and 0.5 ml. of saturated aqueous potassium carbonate solution. The organic layer is separated, dried with anhydrous sodium sulfate and evaporated to dryness under vacuum. The oily residue, containing methyl 10,11-dihydrodibenzo[b.f]thiepin-10-ol-2-acetate-S,S-dioxide (XVII, $R^1$ = Me), is dissolved in 7 ml. of formic acid containing 100 mg. of p-toluenesulfonic acid. The reaction mixture is refluxed for 3 hours, cooled and poured into water. The product is extracted with ethyl acetate, and the organic layer washed with water to neutrality and dried. The resulting solution is decolorized with charcoal and the solvent evaporated to dryness under reduced pressure. Recrystallization of the residue from ethyl acetate affords 640 mg. of dibenzo[b.f]thiepin-2-acetic acid-S,S-dioxide (XVIII), which has a melting point of 162°–163° C.

EXAMPLE 14

A. To a solution of 4 g. of sodium hydride and 20 g. of phenol in 100 ml. of dimethylformamide there are slowly added 50 g. of dimethyl 4-nitroisophthalate. The reaction mixture is stirred for 12 hours at room temperature, poured into 1 l. of water and extracted with ethyl acetate (3 × 100 ml.). The combined extract is washed with water (200 ml.) and dried with anhydrous magnesium sulfate. The solvent is evaporated, and the oily residue is distilled under reduced pressure, to yield 45 g. of dimethyl 4-phenoxyisophthalate, (XX), b.p. 170°/0.2 mm.

B. A solution of 90 g. of dimethyl 4-phenoxyisophthalate in 100 ml. of dimethoxyethane is slowly added to a solution of 25 g. of lithium aluminum hydride in 500 ml. of dimethoxyethane. After 1 hour excess lithium aluminum hydride is destroyed by the slow addition of 50 ml. of saturated aqueous ammonium chloride solution. When the gray reaction mixture becomes white the precipitated metal salts are filtered off and the filtrate is evaporated to dryness. The residue is stirred with 500 ml. of benzene and 3 g. of activated charcoal and warmed on a steam bath for 10 minutes. The solution is filtered and the filtrate is concentrated to about 150 ml. by evaporation, and allowed to crystallize. The crystalline material is separated by filtration, thus obtaining 65 g. of 2,4-bis-(hydroxymethyl)diphenyl ether (XXI), which has a melting point of 73°-74° C.

EXAMPLE 15

A stirred suspension of 60 g. of 2,4-bis-(hydroxymethyl)diphenyl ether in 500 ml. of methylene chloride is treated with 45 ml. of thionyl chloride. After 1 hour the solvent and excess thionyl chloride are evaporated under reduced pressure to give a residue which is filtered through a short column of 50 g. of alumina, eluting with hexane. Evaporation of the eluate affords 63 g. of a colorless oil, which is added to a solution of 25 g. of sodium cyanide in 150 ml. of dimethylformamide. The reaction mixture is stirred at room temperature for 18 hours and then poured into 1.5 l. of water. The resulting suspension is extracted with ethyl acetate (2 × 300 ml.), and the extracts washed with water (200 ml), dried over anhydrous magnesium sulfate, treated with 5 g. of activated charcoal and filtered. Evaporation of the filtrate affords 63 g. of a yellow oil, which is added to a mixture of 120 ml. of acetic acid and 120 ml. of 85% aqueous phosphoric acid. The resulting solution is refluxed for 18 hours, cooled, and poured into 2 l. of 2% aqueous sodium chloride solution. The resulting mixture is cooled to 5° C for 24 hours and the solid material which separates is filtered off, washed with water and dried in vacuum. The crude product is purified by dissolving in 500 ml. of methanol and the solution is saturated with hydrogen chloride. After 3 hours the solution is evaporated under reduced pressure, and the residue extracted with 300 ml. of benzene. The benzene solution is washed with water, dried over anhydrous magnesium sulfate and evaporated. The oily residue is distilled under reduced pressure, to yield 44 g. of a pale yellow oil, b.p. 186°/0.25 mm. This oil is dissolved in 500 ml. of methanol and treated over a period of 30 minutes with 100 ml. of 20% aqueous potassium hydroxide solution. After 1 hour at room temperature the reaction mixture is heated to boiling and 500 ml. of hot (70° C) water is added, to give a clear solution which is acidified with 3N aqueous hydrochloric acid. The resulting solution is cooled to 0° C and the crystalline product is collected by filtration, washed with water and dried in vacuum, thus obtaining 40 g. of 2,4-bis-(carboxymethyl)diphenyl ether (XXII), which melts at 161°-162° C.

EXAMPLE 16

A solution of 15 g. of 2,4-bis-(carboxymethyl)-diphenyl ether in 100 ml. of dimethoxyethane is treated with 20 ml. of oxalyl chloride and the reaction mixture is stirred at room temperature for 48 hours. The solvent and excess oxalyl chloride are evaporated under reduced pressure and the residue is treated with 20 ml. of carbon tetrachloride and again evaporated, to yield an oil. The oil is dissolved in 50 ml. of methylene chloride and added to a solution of 15 g. of aluminum chloride in 300 ml. of methylene chloride containing 15 ml. of nitromethane. The reaction mixture is stirred for 30 minutes at room temperature and then treated with 15 ml. of saturated sodium chloride solution. As soon as the red color of the solution is discharged the mixing is filtered through a bed of Celite, diatomaceous earth. The filtrate is diluted with 50 ml. of methanol, and the solution is refluxed for 10 minutes. The reaction is then cooled and evaporated under reduced pressure. The residue is dissolved in 100 ml. of ethyl acetate and extracted with 10 ml. of 10% aqueous sodium hydroxide. The basic extract is acidified with 3N hydrochloric acid, and the formed precipitate is collected by filtration, washed with water and dried. The crystalline material is recrystallized from ethyl acetatehexane, to give 1.0 g. of 10,11-dihydrodibenzo[b.f]oxepin-10-one-2-acetic acid (XXIII), which has a melting point of 136°-137° C.

The neutral ethyl acetate layer which remains from the basic extraction, is dried with magnesium sulfate and evaporated. The oily residue is chromatographed through a column of 100 g. of silica gel, eluting with ethyl acetate: hexane (1:4). Evaporation of the eluate gives 11.5 g. of methyl 10,11-dihydrodibenzo[b.f]oxepin-10-one-2-acetate (XXIV), a colorless oil having the following physical constants: I.R. $\nu_{max}^{CHCl_3}$ 1740, 1685, 1600 cm$^{-1}$; N.M.R. $\delta_{TMS}^{CDCl_3}$ 3.49 (2H, s), 3.62 (3H, s), 4.00 (2H, s), 7.00-7.80 (5H, m), 7.97 ppm (1H, dd).

EXAMPLE 17

A mixture of 1 g. of methyl 10,11-dihydrodibenzo[b.f]oxepin-10-one-2-acetate, 25 ml. of methanol and 5 ml. of 10% aqueous sodium hydroxide solution is refluxed for 1 hour. The reaction mixture is then cooled and poured into 200 ml. of water. The resulting solution is acidified with 3N hydrochloric acid, and the formed precipitate collected by filtration, washed with water and air dried, thus obtaining 10,11-dihydrodibenzo[b.f]oxepin-10-one-2-acetic acid (XXIII), identical to the product obtained in Example 16.

EXAMPLE 18

To a well stirred solution of 8 g. of methyl 10,11-dihydrodibenzo[b.f]oxepin-10-one-2-acetate in 50 ml. of dimethoxyethane and 25 ml. of methanol there is slowly added 1 g. of sodium borohydride. After 2 hours at room temperature the reaction mixture is concentrated by evaporation under reduced pressure to about 20 ml. and then filtered through 50 g. of silica gel, eluting with hexane:ethyl acetate (2:1). Evaporation of the eluate yields an oil, which is refluxed for 4 hours with 200 ml. of dimethoxyethane containing 2 drops of aqueous 70% perchloric acid. The reaction mixture is then treated with 200 mg. of sodium acetate, cooled, and evaporated under reduced pressure. The residue is chromatographed through 50 g. of silica gel, eluting with hexane:ethyl acetate (8:1). Evaporation of the eluate affords a solid material, which upon recrystallization from hexane yields 4.5 g. of methyl dibenzo[b.f]oxepin-2-acetate (XXV), having a melting point of 76°–77° C.

EXAMPLE 19

A mixture of 2.0 g. of methyl dibenzo[b.f]-oxepin-2-acetate, 50 ml. of methanol and 5 ml. of 2N aqueous potassium hydroxide solution is refluxed for 10 minutes. The reaction mixture is cooled, diluted with 75 ml. of water and filtered through a bed of Celite, diatomaceous earth. The filtrate is heated to 80° C, acidified with 3N hydrochloric acid and allowed to cool. The crystalline material is filtered, washed with water and dried in vacuum, to yield 1.9 g. of dibenzo[b.f]oxepin-2-acetic acid (XXVI), which melts at 187°–188° C.

EXAMPLE 20

A solution of 1.0 g. of dibenzo[b.f]oxepin-2-acetic acid in 50 ml. of dimethoxyethane is stirred for 24 hours in a hydrogen atmosphere with 100 mg. of 10% palladium on charcoal. The catalyst is then removed by filtration and the filtrate evaporated to dryness. Recrystallization of the solid residue from ether:hexane affords 0.85 g. of 10,11-dihydrodibenzo[b.f]oxepin-2-acetic acid, (XXVII), having a melting point of 127°–128° C.

EXAMPLE 21

A solution of 2.2 g. of 10,11-dihydrodibenzo-[b.f]thiepin-2-acetic acid in 20 ml. of dimethoxyethane is treated with ethereal diazomethane until a faint yellow color persists in the solution. The reaction mixture is evaporated to dryness and the residue dissolved in 15 ml. of toluene. The resultant solution is dried by distilling off about 5 ml. of the solvent and then treated with 15 ml. of t-butanol, 6.5 ml. of a solution prepared by dissolving 2 g. of potassium metal in 150 ml. of dry t-butanol, and 1 g. of diethyl carbonate. The reaction mixture is refluxed for 12 hours, 1.0 g. of methyl iodide is then added and the reaction mixture refluxed for a further 4 hours. The solution is cooled and poured into 100 g. of ice containing 2 ml. of concentrated hydrochloric acid. The mixture is then extracted with benzene (2 × 25 ml.), and the combined extracts dried with anhydrous magnesium sulfate and evaporated under reduced pressure. The residue is chromatographed through 25 g. of silica gel, eluting with hexane:ethyl acetate (7:1). Evaporation of the eluate yields 1.3 g. of an oil, which is dissolved in 25 ml. of methanol containing 2 ml. of 50% aqueous potassium hydroxide, and refluxed for 30 minutes. The reaction mixture is cooled and poured into 100 ml. of 1N hydrochloric acid. The mixture is extracted with benzene (2 × 25 ml.), the combined extracts are dried with anhydrous magnesium sulfate and evaporated. The oily residue is dissolved in 5 ml. of benzene and the resultant solution treated with 1 g. of dicyclohexylamine. On standing white crystals of the dicyclohexylammonium salt of (dl) 2-(10,11-dihydrodibenzo[b.f]thiepin-2-yl)propionic acid appear. These are filtered, washed with a little ether and dried, to yield 1.2 g. of dicyclohexylammonium (dl) 2-(10,11-dihydrodibenzo-[b.f]thiepin-2-yl)propionate (XXX, X = S, Z = single bond) which melts at 142°–143° C.

In a similar manner, starting from dibenzo-[b.f]thiepin-2-acetic acid, 10,11-dihydrodibenzo[b.f]oxepin-2-acetic acid,
dibenzo[b.f]oxepin-2-acetic acid,
dibenzo[b.f]thiepin-2-acetic acid-S,S-dioxide,
10,11-dihydrodibenzo[b.f]thiepin-2-acetic acid-S,S-dioxide, and
10,11-dihydrodibenzo[b.f]thiepin-2-acetic acid-S-oxide,
there are respectively obtained:
dicyclohexylammonium (dl) 2-(dibenzo[b.f]thiepin-2-yl)propionate,
dicyclohexylammonium (dl) 2-(10,11-dihydrodibenzo[b.f]oxepin-2-yl)propionate,
dicyclohexylammonium (dl) 2-(dibenzo[b.f]oxepin-2-yl)propionate,
dicyclohexylammonium (dl) 2-(dibenzo[b.f]thiepin-2-yl)propionate-S,S-dioxide,
dicyclohexylammonium (dl) 2-(10,11-dihydrodibenzo[b.f]thiepin-2-yl)propionate-S,S-dioxide and
dicyclohexylammonium (dl) 2-(10,11-dihydrodibenzo[b.f]thiepin-2-yl)propionate-S-oxide.

EXAMPLE 22

A mixture of 500 mg. of dicyclohexylammonium (dl) 2-(10,11-dihydrodibenzo[b.f.]thiepin-2-yl)propionate, 25 ml. of 1N hydrochloric acid and 50 ml. of ether is shaken for 5 minutes. The organic layer is separated, washed with 25 ml. of water and dried with anhydrous magnesium sulfate. Evaporation of the solvent under reduced pressure gives (dl)2-(10,11-dihydrodibenzo[b.f.]thiepin-2-yl)propionic acid (XXXI, X = S, Z = single bond) as a pale yellow oil, NMR: $\delta_{TMS}^{CDCl_3}$ 1.43 (3H, d), 3.30 (4H, s), 3.61 (1H, q), 6.90–7.60 (7H, m), 8.91 ppm (1H, bs).

In a similar manner the remaining dicyclohexylammonium salts obtained in Example 21 are converted into the corresponding free acids, namely:
(dl)2-(dibenzo[b.f]thiepin-2-yl)propionic acid,
(dl) 2-(10,11-dihydrodibenzo[b.f]oxepin-2-yl)propionic acid,
(dl) 2-(dibenzo[b.f.]oxepin-2-yl)propionic acid,
(dl) 2-(dibenzo[b.f]thiepin-2-yl)propionic acid-S,S-dioxide,
(dl) 2-(10,11-dihydrodibenzo[b.f]thiepin-2-yl)propionic acid-S,S-dioxide and
(dl) 2-(10,11-dihydrodibenzo[b.f]thiepin-2-yl)propionic acid-S-oxide.

EXAMPLE 23

A solution of 5 g. of (dl) 2-(10,11-dihydrodibenzo[b.f]thiepin-2-yl)propionic acid in 20 ml. of dimethoxyethane is treated with ethereal diazomethane until a faint yellow color persists in the solution. The reaction mixture is then evaporated to dryness to yield methyl (dl) 2-(10,11-dihydrodibenzo[b.f.]thiepin-2-yl)propionate.

In a similar manner, the remaining compounds obtained in Example 22 are converted into the corresponding methyl esters, namely:
methyl (dl) 2-(dibenzo[b.f]thiepin-2-yl)propionate,
methyl (dl) 2-(10,11-dihydrodibenzo[b.f]oxepin-2-yl)propionate,
methyl (dl) 2-(dibenzo[b.f]oxepin-2-yl)propionate,
methyl (dl) 2-(dibenzo[b.f]thiepin-2-yl)propionate-S,S-dioxide,
methyl (dl) 2-(10,11-dihydrodibenzo[b.f.]thiepin-2-yl)propionate-S,S-dioxide and
methyl (dl) 2-(10,11-dihydrodibenzo[b.f]thiepin-2-yl)propionate-S-oxide.

Likewise, 10,11-dihydrodibenzo[b.f]oxepin-2-acetic acid is converted into its methyl ester.

EXAMPLE 24

By following the method of Example 23 but substituting diazoethane and diazopropane for diazomethane there are obtained ethyl (dl) 2-(10,11-dihydrobenzo[b.f.]-thiepin-2-yl)propionate and propyl (dl) 2-(10,11-dihydrodibenzo[b.f.]thiepin-2-yl)propionate, respectively.

In a similar manner,
10,11-dihydrodibenzo[b.f]thiepin-2-acetic acid-S-oxide,
10,11-dihydrodibenzo[b.f]thiepin-2-acetic acid-S,S-dioxide,
dibenzo[b.f]thiepin-2-acetic acid-S,S-dioxide,
10,11-dihydrodibenzo[b.f]oxepin-2-acetic acid,
dibenzo[b.f]oxepin-2-acetic acid,
(dl) 2-(10,11-dihydrodibenzo[b.f]thiepin-2-yl)propionic acid,
(dl) 2-(dibenzo[b.f]thiepin-2-yl)propionic acid,
(dl) 2-(dibenzo[b.f]oxepin-2-yl)propionic acid,
(dl) 2-(10,11-dihydrodibenzo[b.f]oxepin-2-yl)propionic acid,
(dl) 2-(dibenzo[b.f]thiepin-2-yl)propionic acid-S,S-dioxide,
(dl) 2-(10,11-dihydrodibenzo[b.f]thiepin-2-yl)propionic acid-S-oxide and
10,11-dihydrodibenzo[b.f]thiepin-10-one-2-acetic acid are converted into the corresponding ethyl and propyl esters.

EXAMPLE 25

Examples 7 and 8 are repeated using ethyl 10,11-dihydrodibenzo[b.f]thiepin-10-one-2-acetate as starting material, thus obtaining successively ethyl 10,11-dihydrodibenzo[b.f]thiepin-10-ol-2-acetate, ethyl dibenzo[b.f]thiepin-2-acetate and dibenzo[b.f]thiepin-2-acetic acid, identical to the product obtained in Example 8.

The same compound is obtained as final product using propyl 10,11-dihydrodibenzo[b.f]thiepin-10-one-2-acetate as starting material.

EXAMPLE 26

A solution of 500 mg. of methyl (dl)2-(10,11-dihydrodibenzo[b.f]thiepin-2-yl)propionate in 20 ml. of methylene chloride is treated with 1.1 molar equivalents of m-chloroperbenzoic acid. The reaction mixture is kept at room temperature and then washed with 10% aqueous sodium carbonate solution, dried with anhydrous magnesium sulfate and evaporated to dryness under reduced pressure, to yield methyl (dl) 2-(10,11-dihydrodibenzo[b.f]thiepin-2-yl)propionate-S-oxide.

Likewise but using 2-molar equivalents of m-chloroperbenzoic acid there is obtained methyl (dl) 2-(10,11-dihydrodibenzo[b.f]thiepin-2-yl)propionate-S,S-dioxide.

The foregoing compounds are then hydrolyzed, in accordance with the methods of Examples 10 and 12, respectively, to afford the corresponding free acids, (dl) 2-(10,11-dihydrodibenzo[b.f]thiepin-2-yl)propionic acid-S-oxide and dl 2-(10,11-dihydrodibenzo[b.f]thiepin-2-yl)propionic acid-S,S-dioxide, identical to the products obtained in Example 22.

EXAMPLE 27

A solution of 250 mg. of 10,11-dihydrodibenzo[b.f]-thiepin-2-acetic acid in 30 ml. of isoamyl alcohol is saturated with hydrogen chloride. After 90 minutes, the excess alcohol is distilled off under reduced pressure to yield isoamyl 10,11-dihydrodibenzo[b.f]thiepin-2-acetate, which can be further purified by thin layer chromatography.

Likewise other esters, e.g., isopropyl, cyclopentyl, hexyl, octyl, nonyl, dodecyl, and benzyl, of 10,11-dihydrodibenzo[b.f]thiepin-2-acetic acid are obtained by substituting other alcohols, e.g., isopropyl, cyclopentyl, hexyl, octyl, nonyl, dodecyl, benzyl alcohol and the like, for isoamyl alcohol.

In a similar manner substituting any of the other acids prepared herein for the 10,11-dihydrodibenzo[b.f]thiepin-2-acetic acid there are obtained the corresponding esters, e.g.,
cyclopentyl dibenzo[b.f]thiepin-2-acetate,
hexyl (dl) 2-(10,11-dihydrodibenzo[b.f]thiepin-2-yl)-propionate,
octyl (dl) 2-(dibenzo[b.f]thiepin-2-yl)propionate,
nonyl (dl) 2-(10,11-dihydrodibenzo[b.f]oxepin-2-yl)-propionate,
dodecyl dibenzo[b.f]oxepin-2-acetate,
benzyl 10,11-dihydrodibenzo[b.f]thiepin-2-acetate-S-oxide and
isoamyl 10,11-dihydrodibenzo[b.f]thiepin-2-acetate-S,S-dioxide.

EXAMPLE 28

A solution of 350 mg. of 10,11-dihydrodibenzo[b.f]-thiepin-2-acetic acid in five ml. of methanol is treated with 1.1 molar equivalents of 1N methanolic potassium hydroxide. The solvent is evaporated under reduced pressure and the residue taken up in 2 ml. of methanol, followed by precipitation with ether, to yield potassium 10,11-dihydrodibenzo[b.f]thiepin-2-acetate.

Likewise other salts, e.g., ammonium and sodium, 10,11-dihydrodibenzo[b.f]thiepin-2-acetic acid are prepared by substituting ammonium hydroxide and sodium hydroxide for potassium hydroxide.

In a similar manner, the free acid compounds obtained in Examples 8, 10, 12, 13, 19, 20 and 22 are converted into the corresponding potassium, ammonium and sodium salts.

Representative salts thus obtained are:
sodium dibenzo[b.f]thiepin-2-acetate,
potassium dibenzo[b.f]oxepin-2-acetate,
ammonium 10,11-dihydrodibenzo[b.f]oxepin-2-acetate,
sodium (dl) 2-(10,11-dihydrodibenzo[b.f]thiepin-2-yl)propionate,
potassium (dl) 2-(10,11-dihydrodibenzo[b.f]oxepin-2-yl)-propionate,
ammonium (dl) 2-(dibenzo[b.f]oxepin-2-yl)propionate and
sodium 10,11-dihydrodibenzo[b.f]thiepin-2-acetate-S,S-dioxide.

EXAMPLE 29

Three hundred milligrams of 10,11-dihydrodibenzo[b.f]thiepin-2-acetic acid are dissolved in an excess of 1N aqueous sodium hydroxide and the resultant solution is buffered with 0.3 g. of ammonium chloride. The buffered solution is added to a solution of 200mg. of calcium carbonate in 1N aqueous hydrochloric acid. The formed precipitate is collected by filtration, washed consecutively with water, dimethoxyethane and ether, to yield calcium 10,11-dihydrodibenzo[b.f]-thiepin-2-acetate.

Likewise magnesium 10,11-dihydrodibenzo-[b.f]thiepin-2-acetate is prepared by substituting magnesium carbonate for calcium carbonate.

In a similar manner, the other free acid compounds obtained in Examples 8, 10, 12, 13, 19, 20 and 22 are converted into the corresponding calcium and magnesium salts.

EXAMPLE 30

A solution of 200 mg. of 10,11-dihydrodibenzo-[b.f]thiepin-2-acetic acid in 15 ml. of hot benzene is treated with 60 mg. of isopropylamine. The solution is allowed to cool to room temperature and the crystalline material which forms is collected by filtration, washed with ether and dried, thus obtaining isopropylammonium 10,11-dihydrodibenzo[b.f]-thiepin-2-acetate.

Likewise other amine salts such as diethylamine, ethanolamine, piperidine, tromethamine, choline, and caffeine, of 10,11-dihydrodibenzo[b.f]thiepin-2-acetic acid are prepared by substituting each of the respective amines for isopropylamine.

In a similar manner, the free acid compounds obtained in Examples 8, 10, 12, 13, 19, 20 and 22 are converted into the corresponding amine salts. Representative salts thus prepared are:

diethylamine salt of dibenzo[b.f]thiepin-2-acetic acid,
ethanolamine salt of 10,11-dihydrodibenzo[b.f]thiepin-2-acetic acid-S-oxide,
tromethamine salt of 10,11-dihydrodibenzo[b.f]thiepin-2-acetic acid-S,S-dioxide,
choline salt of dibenzo[b.f]thiepin-2-acetic acid-S,S-dioxide,
caffeine salt of 10,11-dihydrodibenzo[b.f]oxepin-2-acetic acid,
isopropylamine salt of dibenzo[b.f]oxepin-2-acetic acid,
diethylamine salt of 10,11-dihydrodibenzo[b.f]oxepin-2-acetic acid,
tromethamine salt of (dl) 2-(10,11-dihydrodibenzo[b.f]thiepin-2-yl)propionic acid,
caffeine salt of (dl) 2-(10,11-dihydrodibenzo[b.f]oxepin-2-yl)propionic acid and
piperidine salt of (dl) 2-(dibenzo[b.f]thiepin-2-yl)-propionic acid.

What is claimed is:

1. A compound selected from the group of those represented by the formula:

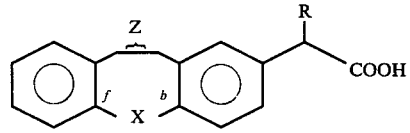

and the pharmaceutically acceptable esters and salts thereof, wherein R is hydrogen or methyl, X is oxygen or $S(O)_n$, in which $n$ is the integer of 0, 1 or 2, and Z is a single or double bond, provided that when Z is a double bond X is not SO, and when R is methyl the compounds are (dl) mixtures.

2. A compound of claim 1 wherein X is $S(O)_n$.

3. A compound of claim 1 wherein X is oxygen.

4. A compound of claim 1 wherein R is hydrogen.

5. A compound of claim 1 wherein R is methyl.

6. A compound of claim 1 wherein Z is a single bond.

7. A compound of claim 1 wherein Z is a double bond.

8. The compound of claim 2 wherein X is S, Z is a single bond and R is hydrogen, 10,11-dihydrodibenzo[b.f]thiepin-2-acetic acid.

9. The methyl ester of the compound of claim 8, methyl 10,11-dihydrodibenzo[b.f]thiepin-2-acetate.

10. The compound of claim 2 wherein X is S, Z is a double bond and R is hydrogen, dibenzo[b.f]thiepin-2-acetic acid.

11. The methyl ester of the compound of claim 10, methyl dibenzo[b.f]thiepin-2-acetate.

12. The compound of claim 2 wherein X is SO, Z is a single bond and R is hydrogen, 10,11-dihydrodibenzo[b.f]thiepin-2-acetic acid-S-oxide.

13. The methyl ester of the compound of claim 12, methyl 10,11-dihydrodibenzo[b.f]thiepin-2-acetate-S-oxide.

14. The compound of claim 2 wherein X is $SO_2$, Z is a single bond and R is hydrogen, 10,11-dihydrodibenzo[b.f]thiepin-2-acetic acid-S,S-dioxide.

15. The methyl ester of the compound of claim 14, methyl 10,11-dihydrodibenzo[b.f]thiepin-2-acetate-S,S-dioxide.

16. The compound of claim 2 wherein X is $SO_2$, Z is a double bond and R is hydrogen, dibenzo[b.f]-thiepin-2-acetic acid-S,S-dioxide.

17. The methyl ester of the compound of claim 16, methyl dibenzo[b.f]thiepin-2-acetate-S,S-dioxide.

18. The compound of claim 3 wherein Z is a single bond and R is hydrogen, 10,11-dihydrodibenzo[b.f]-oxepin-2-acetic acid.

19. The methyl ester of the compound of claim 18, methyl 10,11-dihydrodibenzo[b.f]oxepin-2-acetate.

20. The compound of claim 3 wherein Z is a double bond and R is hydrogen, dibenzo[b.f]oxepin-2-acetic acid.

21. The methyl ester of the compound of claim 20, methyl dibenzo[b.f]oxepin-2-acetate.

22. The compound of claim 2 wherein X is S, Z is a single bond and R is methyl, (dl) 2-(10,11-dihydrodibenzo[b.f]thiepin-2-yl)propionic acid.

23. The dicyclohexylammonium salt of the compound of claim 20, dicyclohexylammonium (dl) 2-(10,11-dihydrodibenzo[b.f]thiepin-2-yl)propionate.

* * * * *